(12) United States Patent
Dieleman

(10) Patent No.: US 7,137,633 B1
(45) Date of Patent: Nov. 21, 2006

(54) WRENCH-FREE MANUAL CHUCK TURBINE

(76) Inventor: John W Dieleman, 500 N. 8th St., Red Oak, IA (US) 51566

( * ) Notice: Subject to any disclaimer, the term of this patent is extended or adjusted under 35 U.S.C. 154(b) by 195 days.

(21) Appl. No.: 10/859,762

(22) Filed: Jun. 4, 2004

(51) Int. Cl.
B23B 31/20 (2006.01)
(52) U.S. Cl. .................... 279/51; 433/127; 433/129
(58) Field of Classification Search .......... 279/42, 279/43.2, 46.1, 46.3, 51, 52, 53; 409/231; 433/129, 132, 126, 127; 415/904
See application file for complete search history.

(56) References Cited

U.S. PATENT DOCUMENTS

| | | | | |
|---|---|---|---|---|
| 3,120,706 A | * | 2/1964 | Turchi et al. .............. 433/129 |
| 3,325,899 A | * | 6/1967 | Staunt ....................... 433/129 |
| 3,499,223 A | * | 3/1970 | Lieb et al. .................. 433/129 |
| 3,521,895 A | | 7/1970 | Smith |
| 3,672,692 A | | 6/1972 | Fauth |
| 3,762,732 A | | 10/1973 | Speed |
| 3,871,097 A | * | 3/1975 | Melde ......................... 433/82 |
| 3,893,242 A | * | 7/1975 | Lieb et al. ................... 433/29 |
| 3,947,966 A | * | 4/1976 | Lieb et al. ................ 433/129 |
| 3,960,039 A | * | 6/1976 | Nash et al. ................. 81/475 |
| 4,015,335 A | * | 4/1977 | Nash et al. ................ 433/127 |
| 4,015,489 A | * | 4/1977 | Lieb et al. ..................... 81/55 |
| 4,249,896 A | * | 2/1981 | Kerfoot, Jr. ................ 433/132 |
| 4,279,597 A | * | 7/1981 | Grimm ....................... 433/129 |
| 4,290,720 A | | 9/1981 | Ferreira |
| 4,313,725 A | * | 2/1982 | Lieb et al. .................. 433/126 |
| 4,595,363 A | * | 6/1986 | Nakanishi ................... 433/129 |
| 4,773,856 A | * | 9/1988 | Mosimann .................. 433/127 |
| 4,966,552 A | * | 10/1990 | Gonser ....................... 433/132 |
| 5,022,857 A | | 6/1991 | Matsutani et al. |
| 5,074,789 A | * | 12/1991 | Shibata ....................... 433/129 |
| 5,252,067 A | * | 10/1993 | Kakimoto ................... 433/129 |
| 5,254,004 A | * | 10/1993 | Feldman et al. ............. 433/129 |
| 5,549,474 A | * | 8/1996 | Cohen ......................... 433/129 |
| 5,779,474 A | * | 7/1998 | Gonser ....................... 433/129 |
| 5,810,588 A | * | 9/1998 | Cohen ......................... 433/129 |
| 5,836,766 A | * | 11/1998 | Gugel et al. ................ 433/127 |
| 5,911,578 A | * | 6/1999 | Gross .......................... 433/127 |
| 6,257,595 B1 | | 7/2001 | Difasi et al. |

* cited by examiner

Primary Examiner—Monica Carter
Assistant Examiner—Michael W. Talbot

(57) ABSTRACT

A manual chuck includes a turbine having a centrally disposed aperture and a spindle including an elongated shaft portion positionable into the aperture in a substantially vertical direction. The spindle further includes a head portion integral with the shaft portion and a centrally disposed aperture formed therein and extending substantially vertically and downwardly through the shaft portion. The chuck function includes a locking member substantially aligned with the spindle aperture and for allowing the chuck to be rotated between predetermined locked and unlocked positions. The chuck further includes a cap for causing the spindle and the locking member to rotate respectively and a plurality of flexible washers disposed between the cap and the locking member.

13 Claims, 3 Drawing Sheets

WRENCH-FREE MANUAL CHUCK TURBINE

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

The present invention relates to wrench-free devices for holding a tool or workpiece on a collet chuck of a rotating turbine and, more particularly, to a wrench-free manual chuck that can be changed quickly and easily.

2. Prior Art

Chucks have commonly been used in machine tools, drills and the like where a workpiece or tool must be grasped and held firmly in place. Unfortunately, conventional jaw chucks have a tendency to loosen their grip at high rotational speeds due to centrifugal force. To combat this tendency, collet chucks are often used. Collet chucks are typically more accurate and have a greater grasping characteristics than typical jaw chucks because they are not affected by centrifugal force. The collet chuck acts as a collar around the workpiece or tool, eliminating any loosening of the grasp.

One problem encountered with collet chucks is that slight variations in the diameter of the workpiece or tool could cause the collet to position the workpiece differently. When and where a collet will grasp a work piece depends on the difference in diameter between the open collet and the diameter of the workpiece. Precise workpiece diameter is therefore required if the workpiece is to be positioned precisely and consistently in machining operations such as facing, side finishing or cutting to precise lengths. Another problem encountered with conventional collet chucks is that the chuck cannot be easily and quickly removed from the spindle. As a result, changing collet chucks can be time consuming and frustrating to users needing to change workpieces frequently, like dentists, for example.

Accordingly, a need remains for a manual chuck with the grasping strength of a collet chuck and the quick release features of a manual jaw chuck.

BRIEF SUMMARY OF THE INVENTION

In view of the foregoing background, it is therefore an object of the present invention to provide a quick turn manual chuck for tightening and loosening a tool or workpiece. These and other objects, features, and advantages of the invention are provided by a wrench-free manual chuck operably connectable to a hand tool turbine bearing for tightening and loosening a burr powered thereby.

The chuck includes a spindle that has an elongated shaft portion positionable into an aperture of the turbine bearing at a substantially vertical direction. The spindle further includes a head portion integral with the shaft portion and has a centrally disposed threaded aperture formed therein that extends substantially vertically and downwardly through the shaft portion and is aligned with the turbine aperture. The spindle head preferably includes a knurled top surface for advantageously maintaining surface contact with the locking member.

The present invention further includes a locking member including a centrally disposed aperture that is substantially aligned with the spindle aperture. The locking member aperture preferably has a sufficient diameter for allowing the pin portion and the chuck member to advantageously rotate therein. The locking member preferably further has a predetermined diameter that is positionable into a predetermined hand tool. The locking member also includes a lower portion that has a pair of opposed flat surfaces formed about a perimeter thereof. The pair of flat surfaces is advantageously engageable with a stationary surface of a hand tool for allowing the chuck to be conveniently rotated between locked and unlocked positions. The flat surfaces of the locking member are preferably diametrically opposed.

The device further includes a hollow chuck member that has a tapered end portion and a threaded end portion secured within the spindle aperture. The tapered end portion is selectively adjustable for receiving and advantageously maintaining a burr at a substantially stable position during operating conditions. The spindle aperture and the chuck member each preferably have a substantially square cross-section so that the pin can be conveniently slidably inserted into the chuck member.

The present invention also includes a cap that has an elongated pin portion extending vertically downwardly therefrom and is selectively positionable into the spindle aperture for engaging the chuck member. The cap preferably has an outer threaded surface or an inner threaded surface so that the end cap can conveniently be threadably secured to a corresponding hand tool. The cap is rotatable between clockwise and counter-clockwise positions for causing the spindle and the locking member to conveniently rotate respectively.

A plurality of spacers are selectively positioned between the turbine bearing and the cap for affectively maintaining a predetermined distance therebtween.

The device also includes a plurality of flexible spring washers formed to be substantially resilient. One spring washer is preferably disposed above the locking member and has a compression force equal to approximately half a compression force of another spring washer disposed below the locking member.

One of the plurality of spring washers allows the cap to be pushed downwardly to position the pin portion into the chuck member. During non-operating conditions this effectively maintains the pin portion disengaged from the chuck member during operating conditions. The other spring washer preferably allows the cap to be engaged with the spindle during non-operating conditions for effectively maintaining the cap disengaged from the spindle during operating conditions. Such a spring washer allows the cap to be pushed downwardly to engage the locking member with the spindle so that the chuck member can conveniently be loosed and tightened, thereby allowing an operator to change a burr connected to the hand tool.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numerals refer to like elements throughout the figures.

Figure 1:
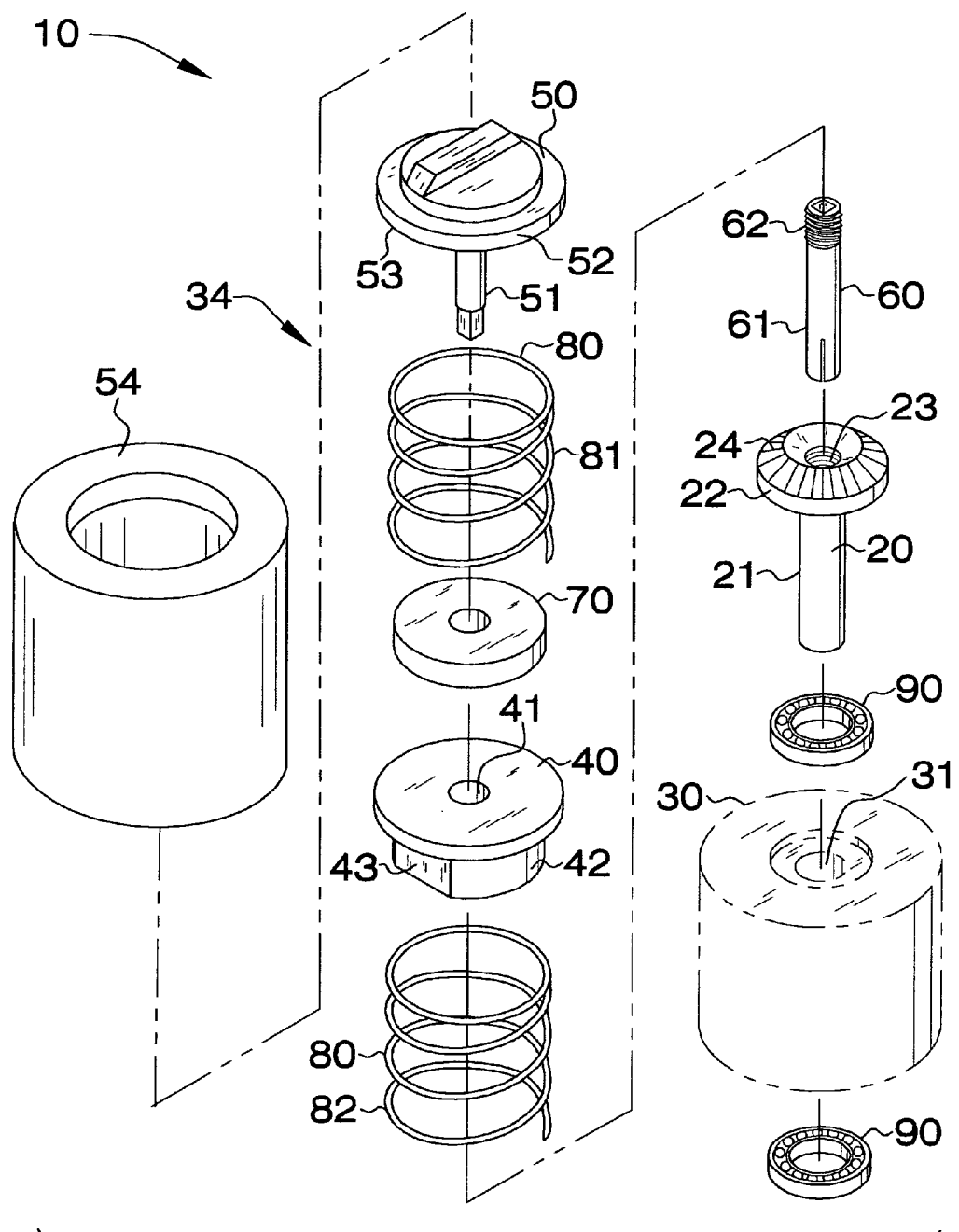
FIG. 1 is an exploded perspective view showing a quick turn manual chuck, in accordance with the present invention.
Figure 2:
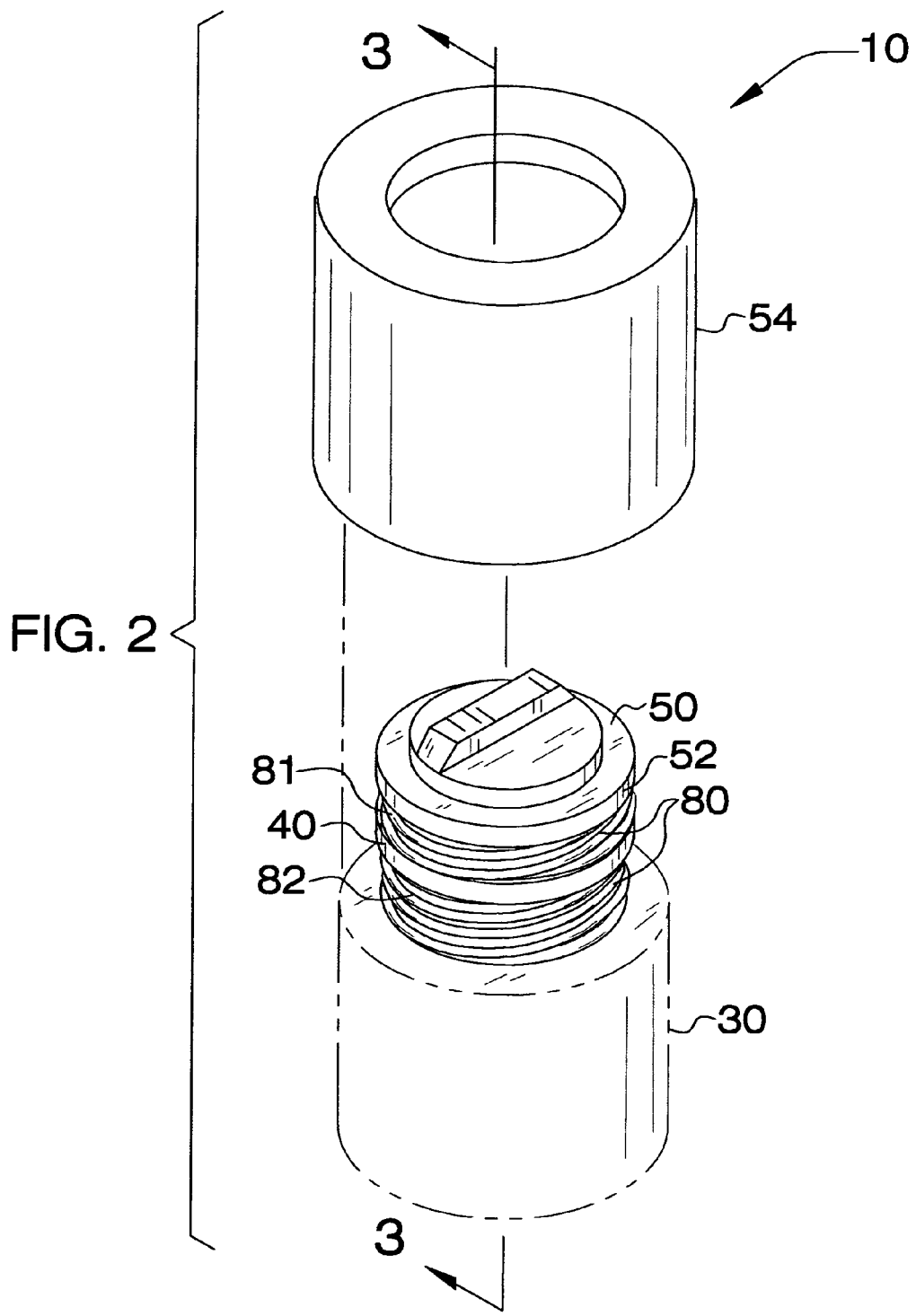
FIG. 2 is an enlarged perspective view of the present invention shown in FIG. 1.
Figure 3:
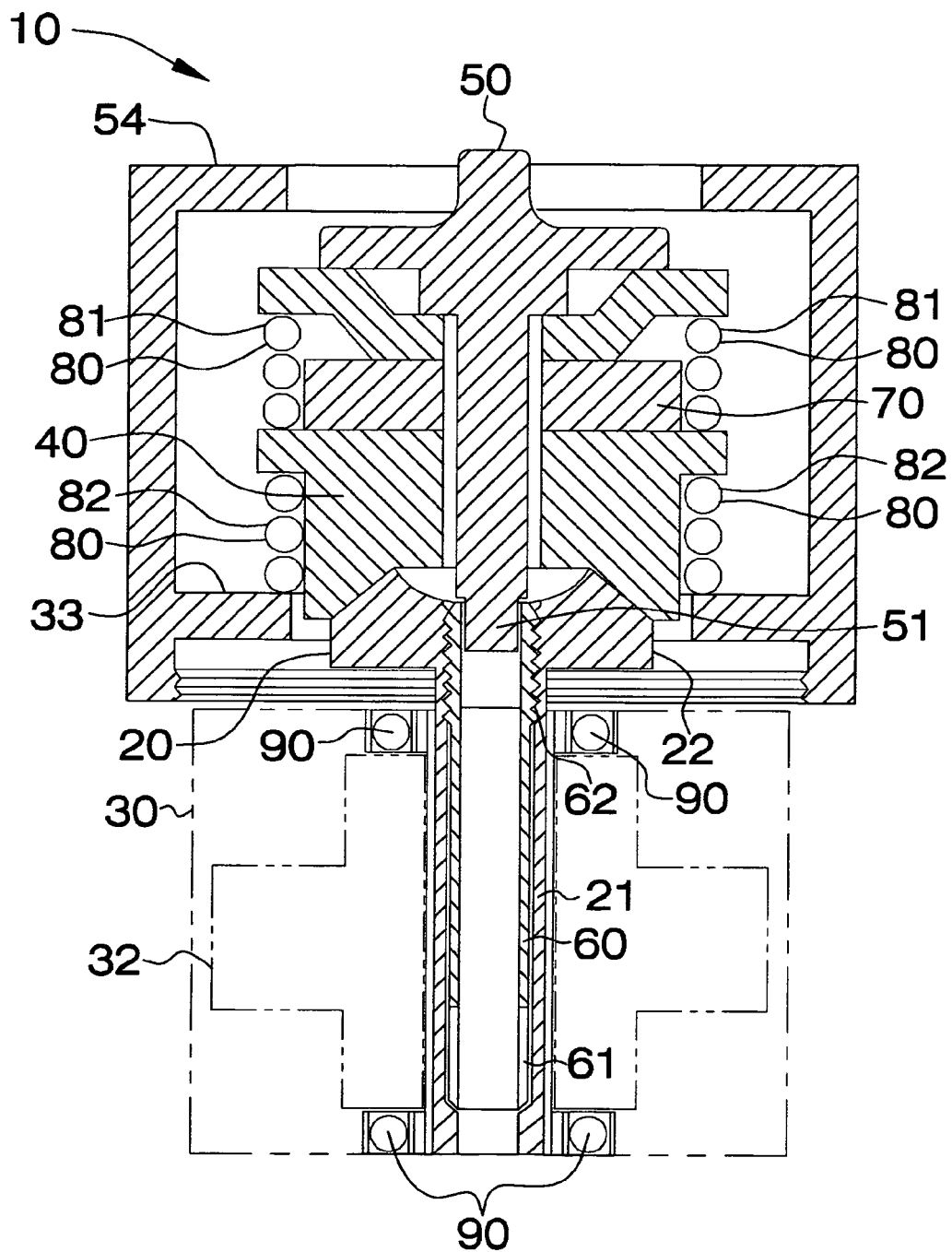
FIG. 3 is a cross-sectional view of FIG. 2, taken along line 3—3.

The device of this invention is referred to generally in FIGS. 1–3 by the reference numeral 10 and is intended to provide a manual chuck that can quickly and easily change a drill bit from a hand-held dental device. It should be understood that the chuck may be used to grasp many different types of tools or workpieces and therefore should not be limited to only dental applications. For example, the present invention may be retrofitted onto conventional wood-carving and automotive tools for operating rotatable bits.

Referring initially to FIG. 1, the device 10 includes a spindle 20 that has an elongated shaft portion 21 positionable into an aperture 31 of the turbine housing 30 at a substantially vertical direction. Of course, it is noted the present invention may employ various conventional turbines including canister and open turbines, for example, as well known to a person of ordinary skill in the art. The spindle 20 further includes a head portion 22 integral with the shaft portion 21 and has a centrally disposed threaded aperture 23 formed therein that extends substantially vertically and downwardly through the shaft portion 21 and is aligned with the turbine bearing aperture 31. The spindle head 22 includes a knurled top surface 24 for advantageously maintaining surface contact with the locking member 40.

The device 10 further includes a plurality of bearings 90 that are disposed above and under the turbine impeller 32. Such bearings 90 help maintain the spindle 20 at a substantially stable position to reduce the usual wear-and-tear caused by operating conditions.

The present invention further includes a locking member 40 including a centrally disposed aperture 41 that is substantially aligned with the spindle aperture 23. The locking member aperture 41 has a sufficient diameter for allowing the pin portion 51 and the chuck member 60 to advantageously rotate therein. The locking member 40 further has a predetermined diameter that is positionable into a predetermined hand piece (not shown). The locking member 40 also includes a lower portion 42 that has a pair of opposed flat surfaces 43 formed about a perimeter thereof. The pair of flat surfaces 43 is advantageously engageable with a stationary surface of a hand tool (not shown) for allowing the chuck 60 to be conveniently rotated between locked and unlocked positions. The flat surfaces 43 of the locking member 40 are diametrically opposed.

The device 10 further includes a hollow chuck member 60 that has a tapered end portion 61 and a threaded end portion 62 secured within the spindle aperture 23. The tapered end portion 61 is selectively adjustable for receiving and advantageously maintaining a burr (not shown) at a substantially stable position during operating conditions. The spindle aperture 23 and the chuck member 60 each have a substantially square cross-section so that the pin 51 can be conveniently slidably inserted into the chuck member 60.

The present invention also includes a cap 50 that has an elongated pin portion 51 extending vertically downward therefrom and is selectively positionable into the spindle aperture 23 for engaging the chuck member 60. The cap 50 has an outer surface 52 and an inner surface 53 so that the manual chuck 60 can be conveniently rotated. In particular, cap 50 rotates inside of housing 54, which has internal or external threads to attach the end cap assembly 34 onto the handpiece (not shown). The cap 50 is rotatable between clockwise and counter-clockwise positions for causing the spindle 20 and the locking member 40 to conveniently rotate respectively.

A plurality of spacers 70 are selectively positioned between the turbine bearing 90 and the cap 50 for affectively maintaining a predetermined distance therebetween.

The device 10 also includes a plurality of flexible spring washers 80 formed to be substantially resilient. One spring washer 81 is disposed above the locking member 40 and has a compression force equal to approximately half a compression force of another spring washer 82 disposed below the locking member 40.

One of the plurality of spring washers 81 allows the cap 50 to be pushed downwardly to position the pin portion 51 into the chuck member 60. During non-operating conditions this effectively maintains the pin portion 51 disengaged from the chuck member 60 during operating conditions. The other spring washer 82 allows the cap 50 to be engaged with the spindle 20 during non-operating conditions for effectively maintaining the cap 50 disengaged from the spindle 20 during operating conditions. Such a spring washer 82 allows the cap 50 to be pushed downwardly to engage the locking member 40 with the spindle 20 so that the chuck member 60 can conveniently be loosed and tightened, thereby allowing an operator to change a burr connected to the hand tool (not shown).

The present invention further includes an end cap housing 54 that effectively covers the cap 50. The end cap 50 assembly 34 is attached by threads to the handpiece (not shown) wherein end cap housing 54 is the housing for the end cap assembly 34, which includes elements 40–43, 50–54, 70, 80–82, and retaining ring 33. Such an end cap assembly 34 is threadably screwed onto the handpiece (not shown). Advantageously, the end cap housing 54 keeps foreign objects, such as dust, out of the assembly 34.

The device 10 combines the convenience of a quick-change chuck with the durability and enhanced reliability of a manual chuck and makes changing tools and workpieces easy and efficient. The major components of the device 10 are preferably formed form medical grade metal similar to that used in conventional dental hand-pieces to prolong product life. The device 10 is particularly well-suited for use by medical professions, such as dentists, who are constantly changing tools while treating patients. The device 10 saves time and money by making such professions more efficient in the use of their time, resulting in better and more cost effective patient care.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new & desired by Letters Patent of the United States is:

1. A manual chuck operably connectable to a turbine and for tightening and loosening a burr powered thereby, said chuck comprising:
    a spindle including an elongated shaft portion positionable into an aperture of said turbine at a substantially vertical direction, said spindle further including a head portion integral with said shaft portion and having a centrally disposed threaded aperture formed therein, said spindle aperture extending substantially vertically and downwardly through said shaft portion and being aligned with said turbine aperture, said spindle aperture being countersunk with a top surface of said head portion, said head portion having an outer perimeter greater than a diameter of said turbine aperture;
    a locking member including a centrally disposed aperture and being substantially aligned with said spindle aperture, said locking member including a lower portion having a pair of opposed flat surfaces formed about a perimeter thereof, said locking member having a diameter greater than a diameter of said head portion and further having a bottom surface directly engaged with said head portion;
    a hollow chuck member having a tapered bottom end portion and a threaded top end portion for being secured within said spindle aperture, said tapered bottom end portion being selectively adjustable for receiving and maintaining a burr at a substantially stable position during operating conditions;
    a cap including an elongated pin portion extending vertically downward therefrom and being selectively positionable into said spindle aperture for engaging said chuck member;
    a plurality of spacers selectively positioned between said turbine aperture and said cap for maintaining a predetermined distance therebetween; and
    a plurality of flexible and coextensively shaped spring washers formed to be substantially resilient, one said plurality of spring washers for allowing said cap to be pushed downwardly to position said pin portion directly into said chuck member, another said plurality of spring washers for allowing said cap to be pushed downwardly to directly engage said locking member with said spindle so that said chuck member can be loosened and tightened and thereby allowing an operator to change a burr;
    wherein said locking member is intercalated between said spring washers such that said locking member maintains direct contact with one of said spacers and said head portion when said chuck member is tightened, said spring washers being vertically aligned and spaced apart during a compressed position.

2. The chuck of claim 1, wherein said spindle aperture and said chuck member each have at least two planar faces registered orthogonal to each other respectively.

3. The chuck of claim 1, wherein said spindle head includes a knurled top surface for maintaining surface contact with said locking member.

4. The chuck of claim 1, wherein one said plurality of spring washers are disposed above said locking member and has a compression force equal to approximately half a compression force of another said plurality of spring washers disposed below said locking member, said one spring washer for allowing an operator to position said pin portion into said chuck member during non-operating conditions and for effectively maintaining said pin portion disengaged from said chuck member during operation conditions, said another spring washer for allowing said cap to be engaged with said spindle during non-operating conditions and for maintaining said cap disengaged from said spindle during operating conditions.

5. The chuck of claim 1, wherein said locking member aperture has a sufficient diameter for allowing said pin portion and said chuck member to rotate therein.

6. A manual chuck for tightening and loosening a burr powered thereby, said chuck comprising:
    a turbine having upper and lower surfaces and a centrally disposed aperture extending therebetween;
    a spindle including an elongated shaft portion positionable into the aperture in a substantially vertical direction, said spindle further including a head portion integral with said shaft portion and having a centrally disposed threaded aperture formed therein, said spindle aperture extending substantially vertically and downwardly through said shaft portion;
    a locking member including a centrally disposed aperture and being substantially aligned with said spindle aperture, said locking member including a lower portion having a pair of opposed flat surfaces formed about a perimeter thereof, said spindle head including a knurled top surface for maintaining surface contact with said locking member;
    a hollow chuck member having a tapered end portion and a threaded end portion for being secured within said spindle aperture, said tapered end portion being selectively adjustable for receiving and maintaining a burr at a substantially stable position during operating conditions;
    a cap including an elongated pin portion extending vertically downward therefrom and being selectively positionable into said spindle aperture for engaging said chuck member;
    a plurality of spacers selectively positioned between said turbine aperture and said cap for maintaining a predetermined distance therebetween; and
    a plurality of flexible spring washers formed to be substantially resilient, one said plurality of spring washers for allowing said cap to be pushed downwardly to position said pin portion into said chuck member, another said plurality of spring washers for allowing said cap to be pushed downwardly to engage said locking member with said spindle so that said chuck member can be loosened and tightened and thereby allowing an operator to change a burr.

7. The chuck of claim 6, wherein said locking member has a predetermined diameter, said flat surfaces of said locking member being diametrically opposed.

8. The chuck of claim 6, wherein one said plurality of spring washers are disposed above said locking member and has a compression force equal to approximately half a compression force of another said plurality of spring washers disposed below said locking member, said one spring washer for allowing an operator to position said pin portion into said chuck member during non-operating conditions and for effectively maintaining said pin portion disengaged from said chuck member during operating conditions, said another spring washer for allowing said cap to be engaged with said spindle during non-operating conditions and for maintaining said cap disengaged from said spindle during operating conditions.

9. The chuck of claim 6, wherein said locking member aperture has a sufficient diameter for allowing said pin portion and said chuck member to rotate therein.

10. A manual chuck for tightening and loosening a burr powered thereby, by said chuck comprising:
  a turbine having upper and lower surfaces and a centrally disposed aperture extending therebetween;
  a spindle including an elongated shaft portion positionable into the aperture in a substantially vertical direction, said spindle further including a head portion integral with said shaft portion and having a centrally disposed threaded aperture formed therein, said spindle aperture extending substantially vertically and downwardly through said shaft portion;
  a locking member including a centrally disposed aperture and being substantially aligned with said spindle aperture, said locking member including a lower portion having a pair of opposed flat surfaces formed about a perimeter thereof, said spindle head including a knurled top surface for maintaining surface contact with said locking member;
  a hollow chuck member having a tapered end portion and a threaded end portion for being secured within said spindle aperture, said tapered end portion being selectively adjustable for receiving and maintaining a burr at a substantially stable position during operating conditions;
  a cap including an elongated pin portion extending vertically downwardly therefrom and being selectively positionable into said spindle aperture for engaging said chuck member;
  a plurality of spacers selectively positioned between said turbine aperture and said cap for maintaining a predetermined distance therebetween; and
  a plurality of flexible spring washers formed to be substantially resilient, one said plurality of spring washers for allowing said cap to be pushed downwardly to position said pin portion into said chuck member, another said plurality of spring washers for allowing said cap to be pushed downwardly to engage said locking member with said spindle so that said chuck member can be loosened and tightened and thereby allowing an operator to change a burr;
  said spindle aperture and said chuck member have coextensively male and female shapes so that said pin can be slidably inserted into said chuck member.

11. The chuck of claim 10, wherein said locking member has a predetermined diameter, said flat surfaces of said locking member being diametrically disposed.

12. The chuck of claim 10, wherein one said plurality of spring washers are disposed above said locking member and has a compression force equal to approximately half a compression force of another said plurality of spring washers disposed below said locking member, said one spring washer for allowing an operator to position said pin portion into said chuck member during non-operating conditions and for effectively maintaining said pin portion disengaged from said chuck member during operating conditions, said another spring washer for allowing said cap to be engaged with said spindle during non-operating conditions and for maintaining said cap disengaged from said spindle during operating conditions.

13. The chuck of claim 10, wherein said locking member aperture has a sufficient diameter for allowing said pin portion and said chuck member to rotate therein.

* * * * *